United States Patent [19]

Iki

[11] Patent Number: 5,548,355
[45] Date of Patent: Aug. 20, 1996

[54] OPHTHALMOLOGIC APPARATUS DETECTING POSITION OF BRIGHT POINTS ON AN EYE TO BE EXAMINED

[75] Inventor: Yoichi Iki, Kawasaki, Japan

[73] Assignee: Nikon Corporation, Tokyo, Japan

[21] Appl. No.: 144,248

[22] Filed: Nov. 1, 1993

[30] Foreign Application Priority Data

Nov. 5, 1992 [JP] Japan .................... 4-296207

[51] Int. Cl.⁶ ........................................... A61B 3/10
[52] U.S. Cl. .................... 351/212; 351/211; 351/221
[58] Field of Search .................... 351/205, 211, 351/212, 221, 247

[56] References Cited

U.S. PATENT DOCUMENTS

| | | | |
|---|---|---|---|
| 4,678,297 | 7/1987 | Ishikawa et al. | 351/208 |
| 4,859,051 | 8/1989 | Fukuma et al. | 351/211 |
| 4,878,750 | 11/1989 | Sekiguchi | 351/212 |
| 4,917,458 | 4/1990 | Matsumura | 351/212 |
| 5,110,200 | 5/1992 | Snook | 351/212 |
| 5,212,507 | 5/1993 | Fujieda et al. | 351/212 |
| 5,214,456 | 5/1993 | Gersten | 351/212 |

FOREIGN PATENT DOCUMENTS 0317768  5/1989  European Pat. Off. .
63-49131  1/1988  Japan .

*Primary Examiner*—William L. Sikes
*Assistant Examiner*—Hung Xuan Dang
*Attorney, Agent, or Firm*—Staas & Halsey

[57] ABSTRACT

The apparatus radiates light onto an eye to be examined and picks up an image of the eye, which is irradiated with light. And then the apparatus compares image information obtained from the image pickup with a threshold determined in advance for the image information so as to store the image information larger than the threshold. The apparatus calculates a measured value of the eye to be examined on the basis of the stored image information.

15 Claims, 9 Drawing Sheets

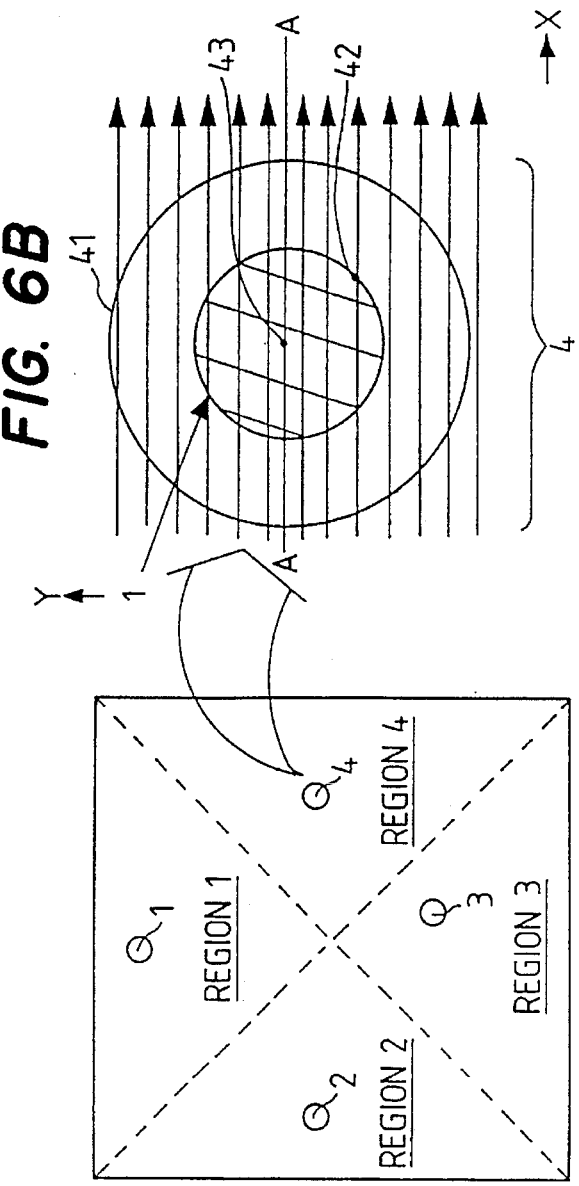
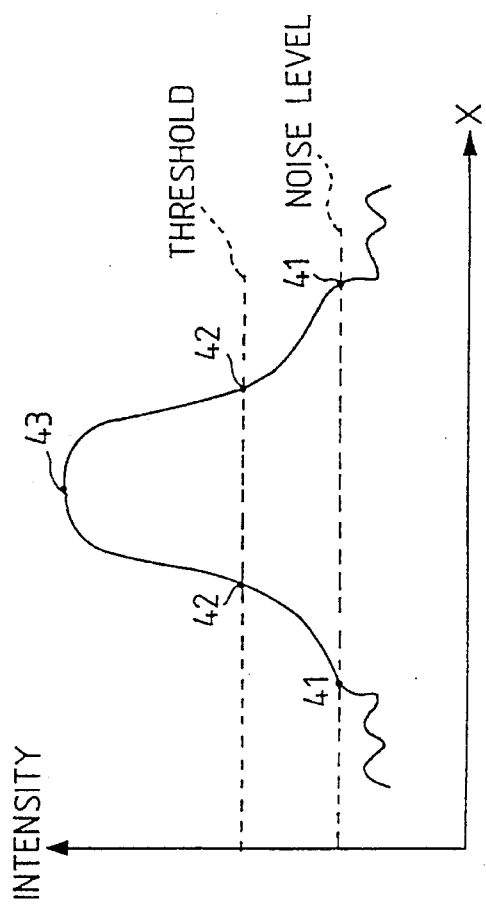
FIG. 6A
FIG. 6B
FIG. 6C

| X<br>Y | 1 | 2 | 3 | 4 |
|---|---|---|---|---|
| 1 | 0 | 1 | 1 | 0 |
| 2 | 1 | 2 | 2 | 1 |
| 3 | 1 | 2 | 2 | 1 |
| 4 | 0 | 1 | 1 | 0 |

OPHTHALMOLOGIC APPARATUS DETECTING POSITION OF BRIGHT POINTS ON AN EYE TO BE EXAMINED

BACKGROUND OF THE INVENTION

1. Field of the Invention

The present invention relates to an ophthalmologic apparatus and, more particularly, to an ophthalmologic apparatus for picking up an image of an eye to be examined, obtaining the position of a bright point formed by a light beam radiated onto the eye to be examined by image processing, and measuring the curvature of a cornea or the eye refracting power.

2. Related Background Art

When the curvature of a cornea or the eye refracting power is measured in an ophthalmologic apparatus, a light beam is radiated onto an eye to be examined, and the position of a bright point (a point illuminated with reflected light) formed by light reflected by the cornea or the fundus of the eye of the radiated light beam must be obtained.

In order to obtain this position, a method of picking up an image of the eye to be examined, and executing image processing is known. At this time, one bright point normally extends over a plurality of pixels.

For this reason, the apparatus comprises a program and an MPU (microprocessor) for obtaining the position of the bright point with high precision, and the program is executed by the MPU. Alternatively, the apparatus may comprise a special-purpose hardware arrangement for realizing this processing.

FIG. 12 is a flow chart showing an example of the program. The operation of this flow chart will be described below.

Pixels for one frame of the eye to be examined are stored in a memory. The memory memorizes luminance data in units of pixels (step S1).

Then, the image of the eye to be examined is divided into a plurality of regions, each of which is expected to include one bright point. The luminance data of all pixels in each region are scanned in units of regions, and are compared with a predetermined threshold to detect pixels exceeding (or equal to or larger than) the threshold. The positions of the detected pixels are memorized (steps S2 to S5).

The centroid of the pixels exceeding (or equal to or larger than) the threshold is calculated for each region, and is determined as the position of the bright point (step S6).

As an example of the special-purpose hardware arrangement, a technique disclosed in Japanese Laid-Open Patent Application No. 63-49131 is known. This special-purpose hardware arrangement stores pixels in an image memory, and at the same time, supplies luminance data and position information of pixels exceeding the threshold to the MPU. The MPU calculates the centroid of pixels exceeding (or equal to or higher than) the threshold for each region, and determines it to be the position of the bright point.

However, in the technique for causing the MPU to execute the program, the luminance data of all pixels must be scanned, and must be compared with a predetermined threshold to detect pixels exceeding (or equal to or higher than) the threshold. For example, in an image defined by 512×512 pixels, the total number of pixels is 262,144, and even if a high-speed MPU is used, too much time is required for processing.

In the example comprising the special-purpose hardware arrangement, the arrangement of the apparatus is complicated, resulting in an expensive apparatus.

SUMMARY OF THE INVENTION

It is an object of the present invention to provide an ophthalmologic apparatus, which can execute processing for detecting the position of a bright point at high speed, and has a simple, inexpensive arrangement of the apparatus.

In order to achieve the above object, there is provided an ophthalmologic apparatus comprising:

radiation means for radiating light onto an eye to be examined;

image pickup means for picking up an image of the eye to be examined, which is irradiated with light emitted from the radiation means;

comparison/memory means for comparing image information obtained from the image pickup means with a threshold determined in advance for the image data, and memorizing the image information larger than the threshold; and calculation means for calculating a measured value of the eye to be examined on the basis of the image information stored in the comparison/memory means.

The comparison/memory means may comprise:

first memory means which stores the threshold;

comparison means for comparing the image information directly input from the image pickup means with the threshold memorized in the first memory means; and second memory means for, when the comparison means determines that the image information is larger than the threshold, memorizing the image information.

The image pickup means may comprise a plurality of pixels, and the comparison/memory means may memorize information associated with at least one pixel from which the image information larger than the threshold is obtained.

Furthermore, the calculation means may calculate the curvature of the cornea of the eye to be examined or the eye refracting power of the eye to be examined.

In the ophthalmologic apparatus of the present invention, required measured values of an eye to be examined, whose image is picked up by the image pickup means, can be calculated at high speed, and the apparatus has a simple, inexpensive arrangement.

BRIEF DESCRIPTION OF THE DRAWINGS

FIGS. 6A–6C are views for explaining an example of the intensity distribution of luminance;

DESCRIPTION OF THE PREFERRED EMBODIMENTS

An embodiment of an ophthalmologic apparatus for obtaining the position of a bright point by image processing according to the present invention will be described below with reference to the accompanying drawings.

In this embodiment, the positions of bright points reflected by the cornea of an eye to be examined are calculated to measure the curvature of the cornea. Also, the present invention can be applied to an ophthalmologic apparatus for measuring the eye refracting power.

Figure 1:
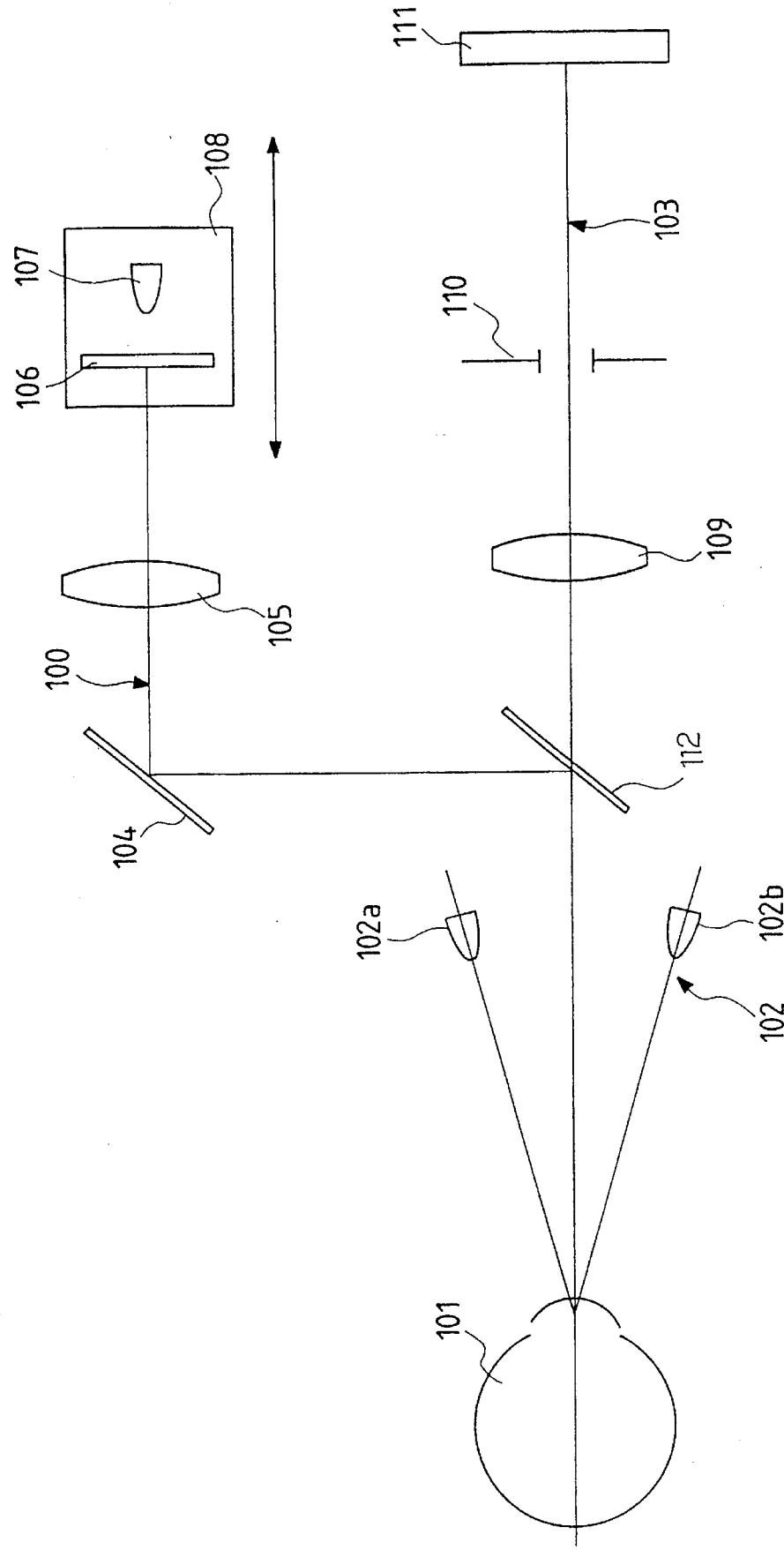
FIG. 1 is a diagram showing an optical system of an ophthalmologic apparatus for measuring the curvature of a cornea according to an embodiment of the present invention.

FIG. 1 shows an optical system of an ophthalmologic apparatus for measuring the curvature of a cornea. The optical system comprises a fixation index optical system 100 for fixing the visual axis of an eye 101 to be examined, an illumination means 102 for radiating a light beam onto the eye 101 to be examined, and an image pickup optical system 103 for forming a cornea reflected image formed by the illumination means 102 on an image pickup unit 111.

The fixation index optical system 100 comprises a total reflection mirror 104, a condenser lens 105, a fixation index 106, and a fixation index illumination light source 107. The fixation index 106 and the fixation index illumination light source 107 are arranged in a fixation index block 108, which is movable in the optical axis direction.

The fixation index illumination light source 107 outputs visible light.

When the fixation index block 108 is moved in the optical axis direction, the diopter of the eye 101 to be examined can be adjusted.

The illumination means 102 comprises four measurement light sources 102a and 102b (the remaining two light sources are not shown) for radiating a light beam onto the eye 101 to be examined.

Each measurement light source preferably outputs infrared rays.

The image pickup optical system 103 comprises a projection lens 109, an aperture 110, and the image pickup unit 111.

A light splitting member 112 for allowing infrared rays to pass therethrough, and reflecting visible light is arranged along the optical axis between the fixation index optical system 100 and the image pickup optical system 103.

In the ophthalmologic apparatus with the above arrangement, light emitted from the fixation index illumination light source 107 is transmitted through the fixation index, and is then radiated onto the eye 101 to be examined via the condenser lens 105, the total reflection mirror 104, and the light splitting member 112.

Then, the fixation index block 108 is moved in the optical axis direction to fix the visual axis of the eye 101 to be examined.

Figure 2:
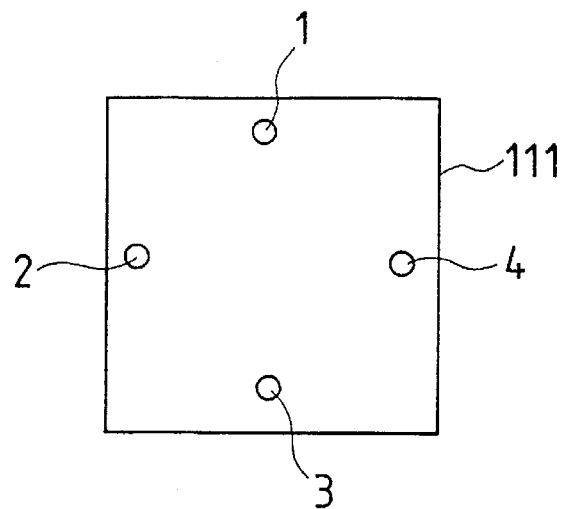
FIG. 2 is a view showing an image picked up by an image pickup unit shown in FIG. 1.

In this state, when infrared rays emitted from the four measurement light sources 102a and 102b are radiated onto the eye 101 to be examined, and an image on the cornea of the eye 101 to be examined is picked up by the image pickup unit 111, a light source image (to be referred to as bright points hereinafter), as shown in FIG. 2, is formed.

The infrared rays forming the bright points are transmitted through the light splitting member 112, and the images of the bright points are formed on the image pickup unit 111 via the projection lens 109 and the aperture 110.

Note that light emitted from the fixation index illumination light source 107 and reflected by the cornea of the eye to be examined is reflected by the light splitting member 112.

Figure 3:
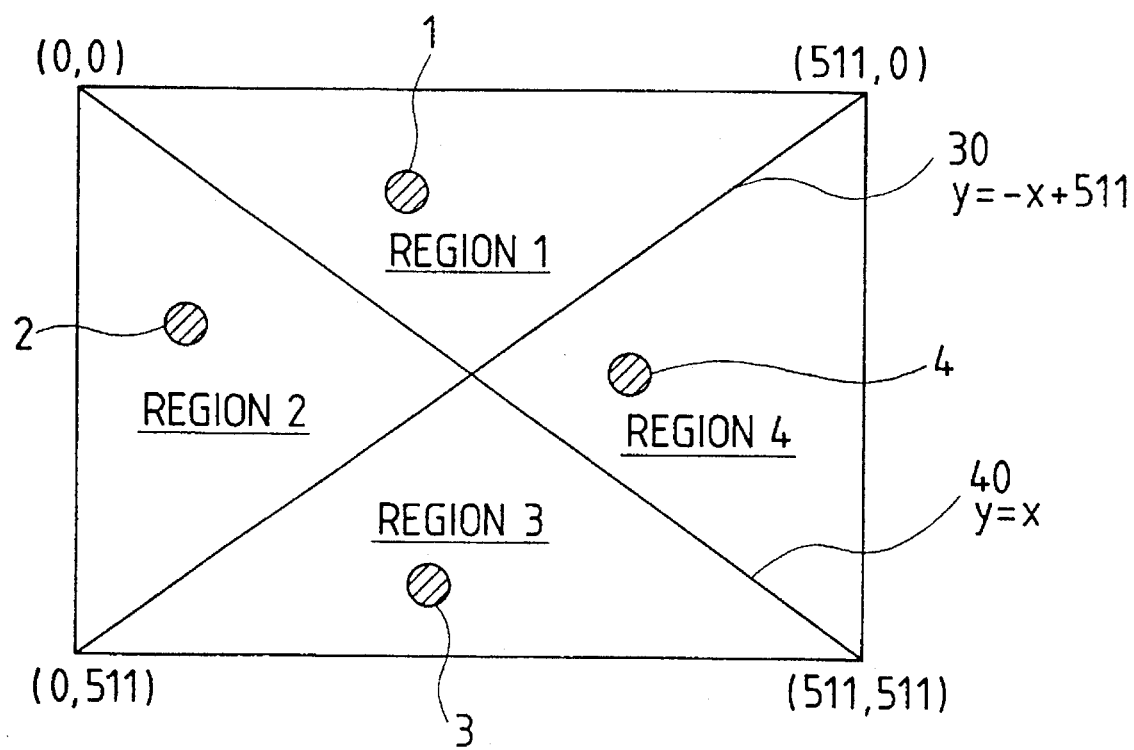
FIG. 3 is an explanatory view of regions and bright points according to the first embodiment of the present invention.

FIG. 3 shows in more detail the four bright points formed on the image pickup unit 111 shown in FIG. 2, and is a view for explaining regions as a plurality of groups, each of which is expected to include one bright point formed by the light beam radiated on the eye to be examined and reflected by the cornea. As shown in FIG. 3, the infrared rays emitted from the measurement light sources 102a and 102b (FIG. 1) are radiated onto the eye 101 to be examined, so that the four bright points (bright points 1 to 4) are included one by one in four groups (to be referred to as regions hereinafter) obtained by dividing an image by two straight lines 30 (y=−x+511) and 40 (y=x).

Figure 4:
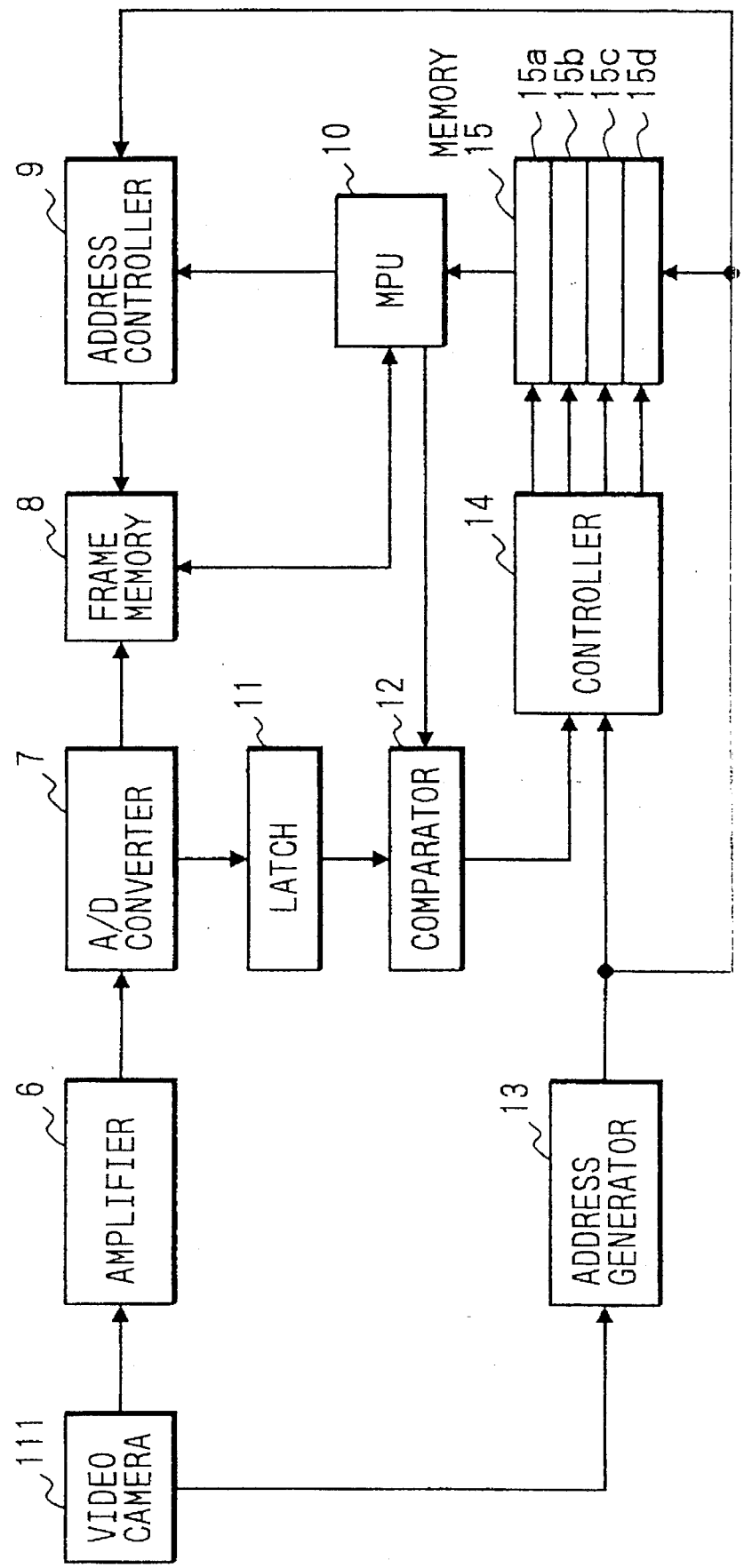
FIG. 4 is a block diagram of a bright point position detection unit according to the first embodiment of the present invention.

FIG. 4 is a block diagram of a portion associated with detection of the positions of bright points (bright point position detection unit) of the ophthalmologic apparatus according to the first embodiment of the present invention.

The bright point position detection unit comprises a video camera 111 as the image pickup unit, an amplifier 6, an A/D converter 7, a frame memory 8, an address controller 9, an MPU (microprocessor unit) 10, a latch 11, a magnitude comparator 12, an address generator 13, an area memory controller 14, and an area memory 15.

The video camera 111 has a plurality of pixels. The image of the eye 101 to be examined is picked up by the video camera 111. The picked-up image signals of the eye 101 to be examined are scanned in turn from the upper left pixel to the lower right pixel of the video camera 111, and are output to the amplifier 6.

A synchronization signal from the video camera 111 is output to the address generator 13. This synchronization signal is a signal representing the pixel of the video camera 111 from which the image signal is being read.

The image signals input to the amplifier 6 are amplified or attenuated, and are then input to the A/D converter 7. Image data which are sequentially converted into digital data by the A/D converter 7 are input to and stored (memorized) in the frame memory 8.

The address generator 13 generates a frame memory address corresponding to the synchronization signal of the pixel which outputs the image signal to the amplifier 6.

The frame memory address is output to the address controller 9 and the area memory 15.

When the image data memorized in the frame memory 8 are read by the MPU 10, the frame memory addresses of required image data are input from the address controller 9 to the frame memory 8.

Conversely, when the MPU 10 memorizes image data in the frame memory 8, the MPU 10 inputs the destination frame memory addresses to the frame memory 8.

The advantage of allowing the MPU 10 to make read/write accesses to the frame memory 8 in this manner will be described later.

On the other hand, the digital image data converted by the A/D converter 7 are held in the data latch 11, and are then input to the magnitude comparator 12. The image data are compared with a threshold set in advance in the MPU 10. As a result of comparison, if image data is larger than the threshold, the area memory controller 14 memorizes the frame memory address at that time in the area memory 15.

Figure 5:
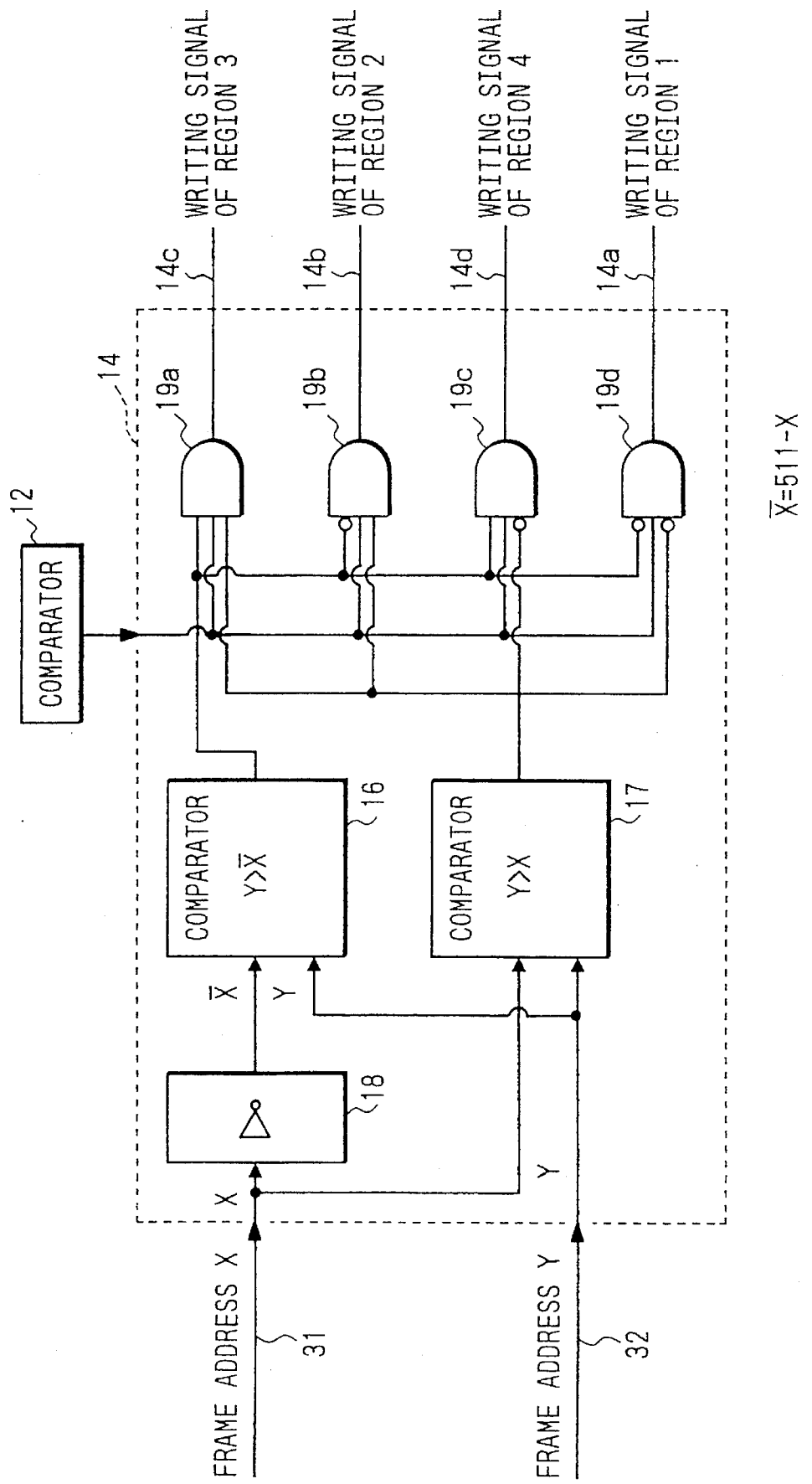
FIG. 5 is a circuit diagram of a memory controller according to the first embodiment of the present invention.

FIG. 5 shows a circuit of the area memory controller 14 associated with write control to the area memory 15.

Referring to FIG. 5, the frame memory address generated by the address generator 13 is output to the area memory controller 14 via a frame memory address X coordinate signal line 31 and a frame memory address Y coordinate signal line 32.

The area memory controller 14 comprises an inverter 18, magnitude comparators 16 and 17, and AND gates 19a, 19b, 19c, and 19d.

The frame memory address X coordinate signal line 31 is connected to the inverter 18 and the magnitude comparator 17, and the frame memory address Y coordinate signal line 32 is connected to the magnitude comparators 16 and 17.

The comparator 16 is connected to the AND gates 19a, 19b, 19c, and 19d, and the comparator 17 is also connected to the AND gates 19a, 19b, 19c, and 19d.

The comparator 12 is also connected to the AND gates 19a, 19b, 19c, and 19d.

In the area memory controller 14 with the above arrangement, each of the X coordinate address output from the frame memory address X coordinate signal line 31, and the Y coordinate address output from the address Y coordinate signal line 32 is set to be 9-bit data so as to assume a value ranging from 0 to 51.

More specifically, if the X coordinate address is represented by an x value, and the x value is inverted by the inverter 18, an $\bar{x}$ value is (511–x).

The comparator 16 receives the $\bar{x}$ value obtained by inverting the X coordinate address, and a y value as the Y coordinate address.

The comparator 17 receives the x value of the X coordinate address, and the y value of the Y coordinate address.

More specifically, when the y value is larger than the $\bar{x}$ value, the comparator 16 outputs an H-level signal (1); otherwise, i.e., when the y value is smaller than the $\bar{x}$ value, the comparator 16 outputs an L-level signal (0).

When the y value is larger than the x value, the comparator 17 outputs an H-level signal (1); otherwise, it outputs an L-level signal (0).

By combining the outputs from these comparators 16 and 17, a signal corresponding to the region (regions 1 to 4) of the frame memory address is obtained.

More specifically, a region above or below the straight lines 30 and 40 (FIG. 3) can be expressed by the outputs from the comparators 16 and 17, and can be classified into the regions 1 to 4.

When the signals from the comparators 16 and 17, and a signal output from the comparator 12 when image data exceeds the threshold are logically ANDed, writing signals 14a, 14b, 14c, and 14d for determining which one of partial memories 15a, 15b, 15c, and 15d of the area memory 15 memorizes the frame memory address are output to the area memory 15.

For example, the frame memory address in the region 1 is memorized in the partial memory 15a; the frame memory address in the region 2 is memorized in the partial memory 15b; the frame memory address in the region 3 is memorized in the partial memory 15c; and the frame memory address in the region 4 is memorized in the partial memory 15d.

In this case, in order to discriminate the boundary between each two adjacent regions, if "<" of the comparator 16 is replaced by "≦", or ">" of the comparator 17 is replaced by, "≧", the boundary can also be detected.

The frame memory address output from the address generator 13 is memorized in one of the partial memories 15a, 15b, 15c, and 15d in correspondence with the writing signals 14a, 14b, 14c, and 14d.

The partial memories 15a, 15b, 15c, and 15d are memories each for memorizing one frame memory address. A new frame memory address is overwritten on the previously memorized frame memory address.

After the image data of the eye 101 to be examined are stored in the frame memory 8, the frame memory addresses of the pixels finally scanned in the corresponding regions of the pixels exceeding the threshold in the corresponding regions are respectively memorized in the partial memories 15a to 15d.

The advantage of allowing the MPU 10 to make read/write accesses of the frame memory 8 is that the MPU 10 can confirm if accurate frame memory addresses are memorized in the area memory 15.

The MPU 10 reads out the frame memory addresses memorized in the partial memories 15a to 15d, and calculates the centroids of the bright points of the corresponding regions on the basis of the readout frame memory addresses.

The method of calculating the centroids will be described later.

FIG. 6 shows the positional relationship between the bright points memorized in the frame memory 8 and the regions, FIG. 6B is an enlarged plan view of one bright point, and FIG. 6B is the light intensity distribution along a line crossing the center of the bright point.

Note that the following description will be made with reference to a point ① (FIG. 6B) in the bright point 4, which point ① is the first scanned point which exceeds the threshold.

Referring to FIG. 6B, arrows illustrated on the enlarged view of the bright point 4 represent scanning lines. In the light intensity distribution along a line A—A on the enlarged view, the intensity of the luminance is highest at a center 43 of the bright point 4, the threshold is equal to the intensity of the luminance at points on circle 42, and the intensity of the luminance exceeds the noise level at points on circle 41. In the case of the bright point 4, the frame memory address of the point ① (of a pixel included therein) in the bright point 4, which point ① is the first scanned point which exceeds the threshold, is stored in the area memory 15d.

In this case, since a theoretical value of the recognition area of the bright point 4 is determined by the radiated light, the centroid of the bright point 4 can be calculated by determining the recognition area of the bright point 4 from, e.g., the radiation magnification of the measurement light sources 102a and 102b.

Figures 7, 8:
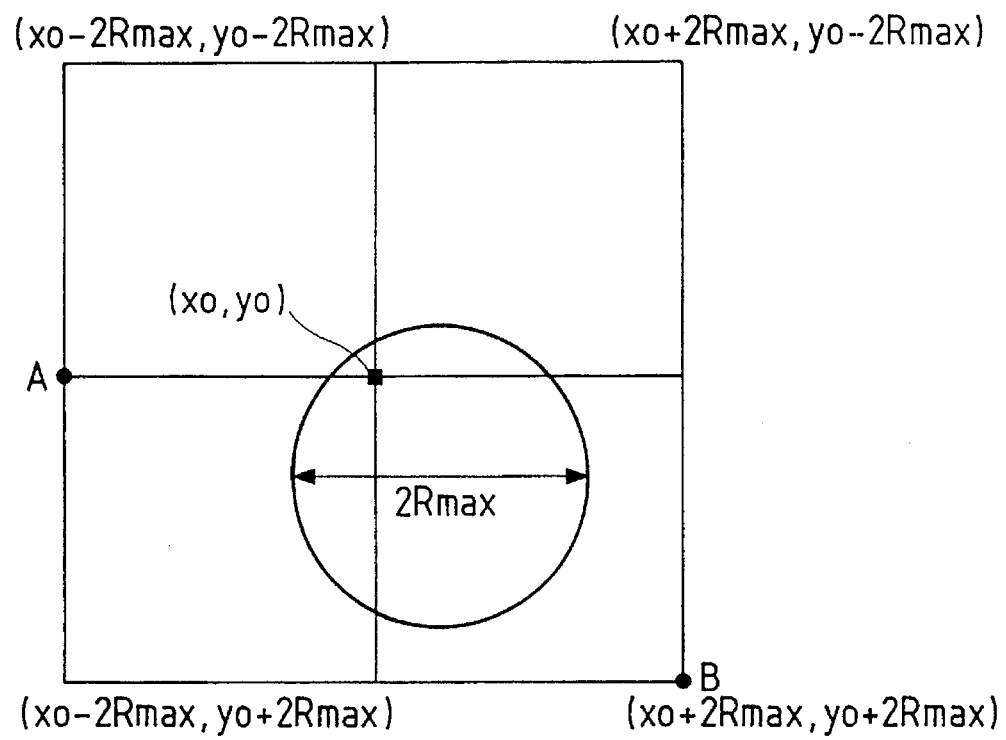
FIG. 7 is a view showing an example for calculating the area of a bright point from one pixel.
FIG. 8 is a view showing an example for calculating the centroid.

For example, as shown in FIG. 7, assume that the diameter of the bright point 4 is 2Rmax when the recognition area has a theoretical maximum value.

When an arbitrary one of pixels present in the bright point is selected, and its coordinates are represented by (x0, y0), as shown in FIG. 7, a square surrounded by coordinates (x0–2Rmax, y0–2Rmax), coordinates (x0+2Rmax, y0–2Rmax), coordinates (x0–2Rmax, y0+2Rmax), and coordinates (x0+2Rmax, y0+2Rmax) with reference to the coordinates (x0, y0) can always include the entire bright point.

This is because the coordinates (x0, y0) represent the point ①, as shown in FIG. 6, and this point corresponds to the coordinate value of the bright point, which value exceeds the threshold first.

When the above-mentioned square is generated based on the coordinates (x0, y0), the square can always include the entire bright point.

Therefore, a square including the bright point is calculated on the basis of the frame memory address which is stored in the area memory 15 and exceeds the threshold first, and the centroid of the bright point can be calculated for all pixels in the square in consideration of the noise level.

Note that the size of the square including the bright point shown in FIG. 7 can be decreased.

More specifically, 2Rmax may be assured from the coordinates (x0, y0) in the obliquely right downward direction (toward a coordinate point B in FIG. 7), and only Rmax may be assured in a direction of a coordinate point A.

In this case, although the square becomes small, the bright point is always included in the square. Since the square is small, the calculation time can be shortened.

When a square which always includes a bright point is calculated, as described above, the image data corresponding to the square are read from the frame memory 8, and the centroid of the bright point is calculated based on the read image data.

A method of calculating the centroid will be described below.

For the sake of simplicity, a case will be described below wherein the centroid of a rectangular region shown in FIG. 8 is to be calculated. The region shown in FIG. 8 includes 16 pixels, and addresses (X coordinate, Y coordinate) of these pixels are (1, 1), (1, 2), (1, 3), (1, 4), (2, 1), (2, 2), (1, 4), (2, 4), (3, 4), and (4, 4), and luminance data of these pixels are respectively 0, 1, 1, 0, 1, 2, 2, 1, 1, 2, 2, 1, 0, 1, 1, and 0 in turn.

In the region shown in FIG. 8, for example, the noise level is defined to be 1. The address of a pixel whose luminance is equal to or higher than the noise level is represented by (Xi, Yj) (for each of i and j is one of 1, 2, 3, and 4), and the luminance at the address (Xi, Yj) is represented by Pij. At this time, if the centroid of this rectangular region is represented by (X0, Y0), X0 and Y0 are calculated as follows. More specifically, the centroid is (2.5, 2.5).

$$X0 = \frac{\sum_i Xi \cdot Pij}{\sum_i Pij}$$

$$Y0 = \frac{\sum_i Yi \cdot Pij}{\sum_i Pij}$$

$$X0 = \frac{(2 \cdot 1 + 3 \cdot 1 + 1 \cdot 1 + 2 \cdot 2 + 3 \cdot 2 + 4 \cdot 1 + 1 \cdot 1 + 2 \cdot 2 + 3 \cdot 2 + 4 \cdot 1 + 2 \cdot 1 + 3 \cdot 1)}{(1 + 1 + 1 + 2 + 2 + 1 + 1 + 2 + 2 + 1 + 1 + 1)}$$

$$= \frac{40}{16}$$

$$= 2.5$$

$$Y0 = \frac{(1 \cdot 1 + 1 \cdot 1 + 2 \cdot 1 + 2 \cdot 2 + 2 \cdot 2 + 2 \cdot 1 + 3 \cdot 1 + 3 \cdot 2 + 3 \cdot 2 + 3 \cdot 1 + 4 \cdot 1 + 4 \cdot 1)}{(1 + 1 + 1 + 2 + 2 + 1 + 1 + 2 + 2 + 1 + 1 + 1)}$$

$$= \frac{40}{16}$$

$$= 2.5$$

Note that the memories 15a to 15d may store only the addresses at which the value of data exceeds the threshold finally in each region.

Figure 9:
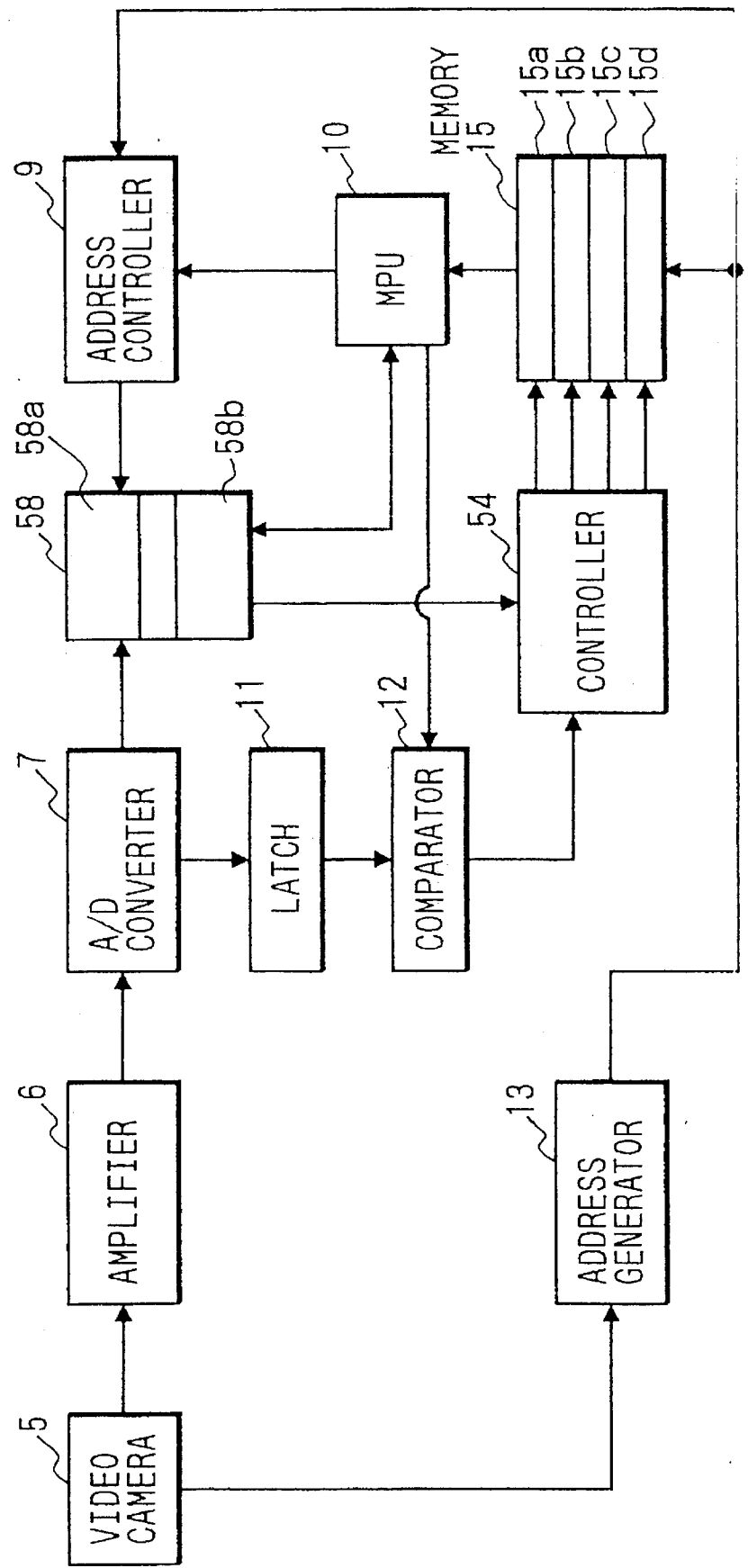
FIG. 9 is a block diagram of a bright point position detection unit according to the second embodiment of the present invention.

FIG. 9 is a block diagram of a portion associated with detection of the positions of bright points (bright point position detection unit) of the ophthalmologic apparatus according to the second embodiment of the present invention.

In the first embodiment, the shapes of the regions 1 to 4 are fixed to those shown in FIG. 3. However, in the second embodiment, the regions 1 to 4 can be set to have complicated shapes. A difference between the second and first embodiment is that a frame memory 58 comprises an image data memory section 58a and a region memory section 58b, and an area memory controller 54 writes addresses in the memories 15a to 15d corresponding to regions designated by the region memory section 58b.

Figure 10:
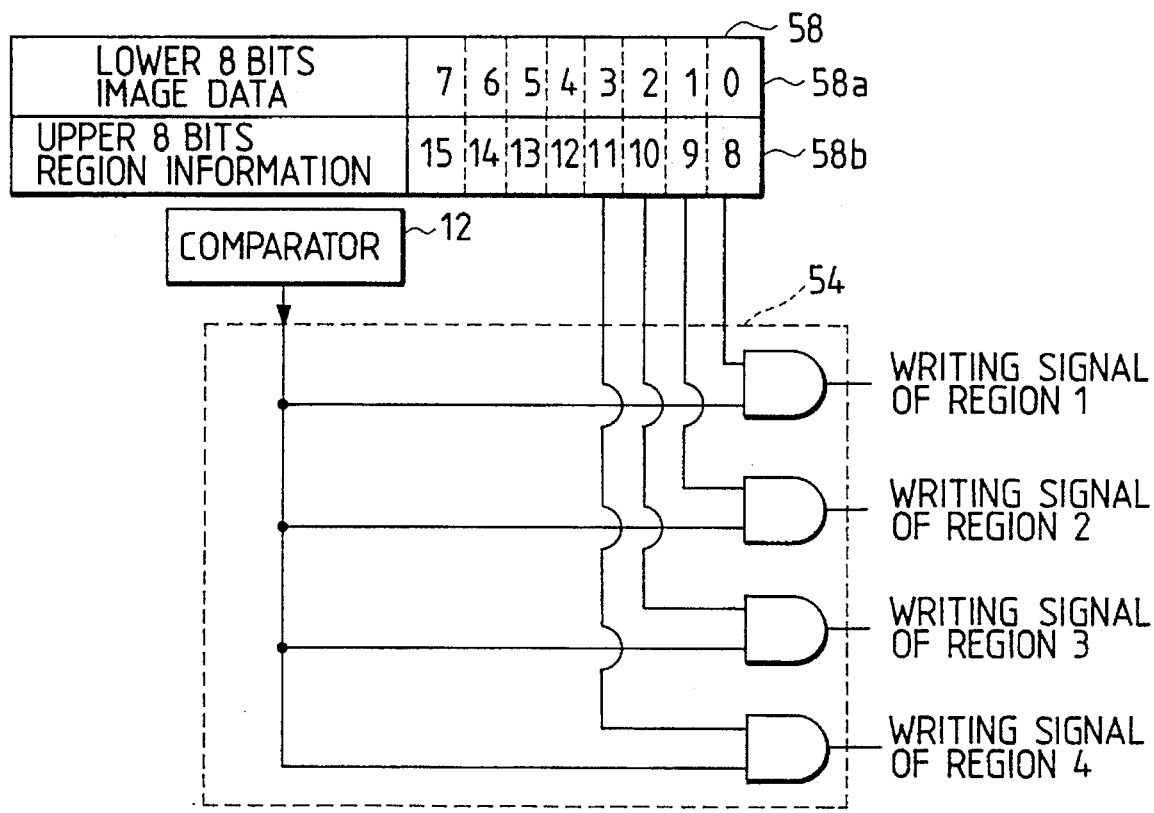
FIG. 10 is a circuit diagram of a memory controller according to the second embodiment of the present invention.

FIG. 10 shows a circuit of the area memory controller 54 associated with write control to the memory 15, and the memory formats of the image data memory section 58a and the region memory section 58b of the frame memory 58.

The frame memory 58 stores pixel data (luminance information) of pixels and region information (information indicating the regions 1 to 4). As shown in FIG. 10, the frame memory 58 stores one address as 16-bit data. The lower 8 bits (bits 0 to 7) of the 16-bit data store image data as the image data memory section 58a, and the upper 8 bits (bits 8 to 15) store region information as the region memory section 58b.

Of the region information of the upper 8 bits, bits 12 to 15 are undefined bits to provide versatility. Bits 8 to 11 respectively correspond to the regions. That is, if bit 8=1, it indicates a pixel of the region 1; if bit 9=1, a pixel of the region 2; if bit 10=1, a pixel of the region 3; and if bit 11=1, a pixel of the region 4. Information indicating the region where the corresponding pixel is present is written in advance in the region memory section 58b, and the information indicating the region is read by the controller 54 while storing image data.

Which partial memory of the area memory 15 memorizes the frame memory address output from the address generator 13 is determined based on the bit indicating the area, which bit is read out by the controller 54.

With this arrangement, a circuit for determining the region to which a pixel belongs can be omitted unlike in the first embodiment. Also, a region having a complicated shape can be set. Furthermore, the shape of the region can be easily changed.

Figure 11:
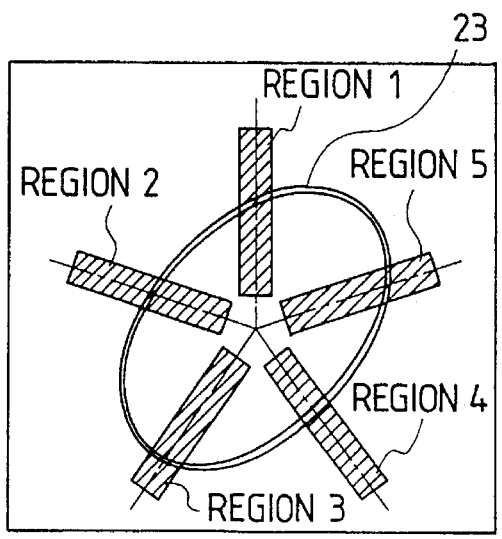
FIG. 11 is a view showing a setting example of regions for an ellipse.
Figure 12:
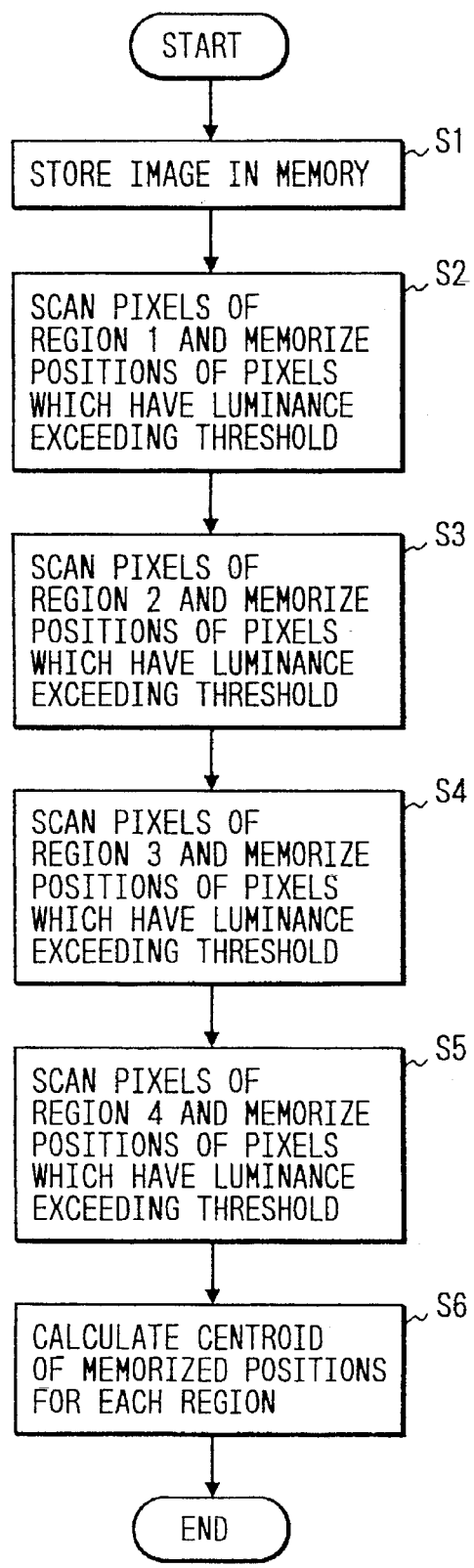
FIG. 12 is a flow chart of a conventional program.

In this embodiment, the centroids of the four bright points are calculated. However, the present invention can be applied to detection of a larger number of bright points, as a matter of course. Also, the present invention can be applied to a case wherein a ring image is projected onto the cornea or the fundus of the eye in place of bright points, and an equation of ellipse is obtained from the projected image. In order to obtain the equation of ellipse, the coordinates of five points on an ellipse need only be obtained. Therefore, as shown in FIG. 11, five regions are set for an ellipse 23, and the address at which the luminance exceeds the threshold can be detected for each region.

A further detailed description about FIG. 11 will be given below. Referring to FIG. 11, a light source having a pattern (circular pattern) formed with a circular light-shielding portion is used as the illumination means 102, and the circular pattern is projected onto the eye to be examined. A circular pattern image reflected by the eye to be examined is an ellipse 23, as shown in FIG. 11.

The curvature of the cornea is then calculated based on the circular pattern and the ellipse 23.

When the curvature of the cornea is calculated, five regions each having a predetermined width are set on the ellipse 23 at equal angular intervals.

As the width of the region is smaller, the number of points crossing the ellipse 23 becomes smaller, and the calculation processing speed can be increased.

Therefore, in the following description, each region is defined by a line segment.

More specifically, the addresses of pixels of the ellipse 23, which pixels cross the regions, are obtained, and when the equation of ellipse is obtained based on the addresses of these pixels, the curvature of the eye to be examined can be calculated.

Note that the regions need not always be set at equal angular intervals.

The frame memory 8 is not always needed in the present invention. Even when the frame memory 8 is omitted, image data exceeding the threshold, and the addresses of the image data can be detected.

However, when the frame memory 8 is arranged, it can be confirmed if the image data exceeding the threshold, and the addresses of the image data coincide with each other, and the measured values of the eye to be examined can be calculated while displaying an image on a TV screen.

In place of the frame memory 8, an observation optical system may be added to the ophthalmologic apparatus.

What is claimed is:

1. An ophthalmologic apparatus comprising:

radiation means for radiating light onto an eye to be examined;

image pickup means for obtaining image information representing an image of the eye to be examined, the image including the light emitted from said radiation means after reflection by the eye to be examined;

comparison/memory means for comparing the image information, as the image information is obtained by said image pickup means, with a threshold determined in advance for the image information, and storing the image information when the threshold is exceeded; and calculation means for calculating a measured value of the eye to be examined on the basis of the image information stored in said comparison/memory means.

2. An apparatus according to claim 1, wherein said comparison/memory means comprises:

first memory means for storing the threshold;

comparison means for comparing the image information directly input from said image pickup means with the threshold stored in said first memory means; and second memory means for storing the image information when said comparison means determines that the image information exceeds the threshold.

3. An apparatus according to claim 1, wherein said image pickup means comprises an input device producing the image information for a plurality of pixels forming the image of the eye to be examined, and wherein said comparison/memory means stores information associated with at least one pixel from which the image information exceeding the threshold is obtained.

4. An apparatus according to claim 1, wherein said calculation means calculates at least one of a curvature of a cornea of the eye to be examined and an eye refracting power of the eye to be examined.

5. An ophthalmologic apparatus comprising:

radiation means for radiating a plurality of light beams onto an eye to be examined;

image pickup means for obtaining image information, including luminance data, for a plurality of pixels forming an image including bright points of the eye to be examined, the bright points being generated when the plurality of light beams are reflected by the eye to be examined;

a frame memory for storing the image information for the pixels obtained by said image pickup means;

classification means for classifying the image information obtained from said image pickup means into a plurality of groups each including one bright point;

memory means for storing thresholds determined in correspondence with the groups;

holding means for comparing the luminance data of the image information for the pixels obtained by said image pickup means with a corresponding one of the thresholds, and for holding an address in said frame memory of at least one pixel having the luminance data exceeding the threshold, in units of the groups classified by said classification means; and calculation means for calculating a measured value of the eye to be examined based on the addresses held in said holding means.

6. An apparatus according to claims 5, wherein the at least one pixel having the luminance data exceeding the threshold is included in one of the bright points.

7. An apparatus according to claim 5, wherein said classification means comprises group information determination means for determining which one of the groups corresponds to the image information, when the image information is stored in said frame memory, and wherein said holding means comprises control means for controlling the holding of the address of the at least one pixel to hold the address of the at least one pixel in the one of groups in accordance with the group information.

8. An apparatus according to claim 5, wherein said calculation means calculates a rectangular region including one of the bright points based on the address of the at least one pixel stored in said holding means and an arbitrary condition of said radiation means, reads out the image information for the rectangular region from said frame memory, and calculates a centroid of the one of the bright points for calculation of the measured value of the eye to be examined.

9. An ophthalmologic apparatus comprising:

radiation means for radiating a light beam onto an eye to be examined;

image pickup means for obtaining image information, including luminance data, for a plurality of pixels forming an image including bright points of the eye to be examined, the bright points being generated when the light beam is reflected by the eye to be examined;

a frame memory for storing the image information for the pixels obtained by said image pickup means;

comparison means for comparing the luminance data of the image information for the pixels obtained by said image pickup means with a threshold determined in advance for the luminance data;

assuring means for assuring an address of said frame memory in accordance with at least one pixel determined by said comparison means to have the luminance data exceeding the threshold;

bright point prediction/memory means for predicting and storing a size of the bright points generated by the light beam;

pixel selection means for selecting a group of the pixels near the address of said frame memory based on the size of the bright points stored in said bright point prediction/memory means;

extraction means for extracting the at least one pixel having the luminance data exceeding the threshold from the group of the pixels selected by said pixel selection means; and calculation means for calculating a position of a centroid of one of the bright points based on the at least one pixel extracted by said extraction means for obtaining a measured value of the eye to be examined.

10. An apparatus according to claim 9, wherein said comparison means compares the luminance data of the image information obtained from each pixel of said image pickup means with the threshold for the luminance data when the image information is stored in said frame memory.

11. An ophthalmologic apparatus comprising:

a light source to radiate light onto an eye to be examined;

a camera to obtain image information from light reflected by the eye to be examined, the image information including luminance data;

a comparator to compare the luminance data of the image information obtained by said camera with a threshold determined in advance for the luminance data of the image information;

an area memory to store the image information corresponding to the luminance data when said comparator determines that the luminance data exceeds the threshold; and a calculator to calculate a measured value of the eye to be examined based on the image information stored in said area memory.

12. An apparatus according to claim 11, wherein said camera comprises a video camera, wherein said apparatus further comprises a frame memory to store the image information obtained by said video camera, and wherein said comparator compares the luminance data of the image information obtained by said camera with the threshold determined in advance for the luminance data of the image information upon storing the image information in said frame memory.

13. An apparatus according to claim 11, further comprising a frame memory which stores said image information obtained by said camera, wherein said camera obtains a plurality of pixels included in the image information, based on the light emitted from said light source after reflection by the eye to be examined, wherein said comparator obtains a comparison result by comparing the luminance data of the image information obtained by said camera with the threshold determined in advance for the luminance data of the image information upon storing the image information in said frame memory, wherein said area memory stores an address in said frame memory of at least one pixel having the luminance data exceeding the threshold based on the comparison result obtained by said comparator, and wherein said calculator calculates a measured value of the eye to be examined based on the address stored in said area memory and the image information stored in said frame memory.

14. An apparatus according to claim 13, wherein the image information obtained by said camera represents an image including bright points of the eye to be examined, the bright points being formed by the light emitted from said light source after reflection by at least one of a fundus oculi and a cornea of the eye to be examined.

15. An apparatus according to claim 13, further comprising a converter to convert analog data representing the image information obtained by said camera into digital data;

wherein said frame memory stores the digital data after conversion by said converter, wherein said comparator compares the digital data with the threshold when the digital data is stored in said frame memory, wherein said area memory stores the address in said frame memory of the digital data having a value exceeding the threshold based on the comparison result of said comparator, and wherein said calculator calculates the measured value of the eye to be examined based on the address stored in said area memory and the digital data stored in said frame memory.

* * * * *